US006609027B2

United States Patent
Kroll et al.

(10) Patent No.: US 6,609,027 B2
(45) Date of Patent: Aug. 19, 2003

(54) HIS BUNDLE SENSING DEVICE AND ASSOCIATED METHOD

(75) Inventors: Mark W. Kroll, Simi Valley, CA (US); John R. Helland, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 211 days.

(21) Appl. No.: 09/793,640

(22) Filed: Feb. 23, 2001

(65) Prior Publication Data

US 2002/0120318 A1 Aug. 29, 2002

(51) Int. Cl.[7] .............................................. A61N 1/368
(52) U.S. Cl. ........................................................ 607/9
(58) Field of Search ............................ 607/4, 9, 14, 17, 607/18, 19, 24–28

(56) References Cited

U.S. PATENT DOCUMENTS

| | | | | |
|---|---|---|---|---|
| 4,577,634 A | * | 3/1986 | Gessman | 607/14 |
| 4,953,564 A | * | 9/1990 | Berthelsen | 607/120 |
| 5,306,292 A | | 4/1994 | Lindegren | 607/11 |
| 5,320,642 A | * | 6/1994 | Scherlag | 607/9 |
| 5,466,245 A | | 11/1995 | Spinelli et al. | 607/17 |
| 5,514,163 A | | 5/1996 | Markowitz et al. | 607/9 |
| 5,540,727 A | | 7/1996 | Tockman et al. | 607/18 |
| 5,584,868 A | | 12/1996 | Salo et al. | 607/17 |
| 5,645,580 A | | 7/1997 | Moaddeb et al. | 607/122 |
| 5,683,447 A | * | 11/1997 | Bush et al. | 607/126 |
| 5,692,907 A | | 12/1997 | Glassel et al. | 434/262 |
| 5,700,283 A | | 12/1997 | Salo | 607/17 |
| 5,800,471 A | | 9/1998 | Baumann | 607/25 |
| 5,902,324 A | * | 5/1999 | Thompson et al. | 607/9 |

OTHER PUBLICATIONS

Deshmukh, Pramod, M.D., "Permanent, Direct His–Bundle Pacing. A Novel Approach to Cardiac Pacing in Patients With Normal His–Purkinjie Activation," Circulation, pp 869–877, (Feb. 29, 2000).

* cited by examiner

Primary Examiner—Kennedy Schaetzle
Assistant Examiner—Kristen Droesch

(57) ABSTRACT

A cardiac stimulation device, a His Bundle lead, and an associated method for detecting a conduction signal from the His Bundle. Upon this detection, the stimulation device delivers ventricular stimulation to the right and/or left ventricles at an interval following the atrial depolarization. A sensing window is initiated following the sensing of the atrial depolarization. During the sensing windows, the His Bundle signal received through the His Bundle lead is sampled and a moving average is calculated to determine a signal peak. Detection of the His Bundle signal peak triggers ventricular stimulation, which may be delivered to the right ventricle, the left ventricle, or both ventricles.

45 Claims, 9 Drawing Sheets

HIS BUNDLE SENSING DEVICE AND ASSOCIATED METHOD

FIELD OF THE INVENTION

This invention relates generally to implantable cardiac stimulating devices. More specifically, the present invention is directed to a dual-chamber cardiac stimulation device using a lead designed for locating the His Bundle, for fixation to the site of the His Bundle, and for sensing a His Bundle signal. This invention further relates to a method for delivering ventricular stimulation at an optimal atrioventricular delay in patients with bundle branch conduction abnormalities.

BACKGROUND OF THE INVENTION

In a normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (AV) node and a ventricular conduction system comprised of the bundle of His, the left and right bundle branches, and the Purkinje fibers causing a depolarization known as an R-wave and the resulting ventricular chamber contractions.

Disruption of this natural pacemaking and conduction system as a result of aging or disease can be successfully treated by artificial cardiac pacing using implantable cardiac stimulation devices, including pacemakers and implantable defibrillators, which deliver rhythmic electrical pulses or other anti-arrhythmia therapies to the heart, via electrodes implanted in contact with the heart tissue, at a desired energy and rate. One or more heart chambers may be electrically stimulated depending on the location and severity of the conduction disorder.

A single-chamber pacemaker delivers pacing pulses to one chamber of the heart, either one atrium or one ventricle. Dual chamber pacemakers are now commonly available and can provide stimulation in both an atrial chamber and a ventricular chamber, typically the right atrium and the right ventricle. Both unipolar or bipolar dual chamber pacemakers exist in which a unipolar or bipolar lead extends from an atrial channel of the dual chamber device to the desired atrium (e.g. the right atrium), and a separate unipolar or bipolar lead extends from a ventricular channel to the corresponding ventricle (e.g. the right ventricle). In dual chamber, demand-type pacemakers, commonly referred to as DDD pacemakers, each atrial and ventricular channel includes a sense amplifier to detect cardiac activity in the respective chamber and an output circuit for delivering stimulation pulses to the respective chamber.

If an intrinsic atrial depolarization signal (e.g. a P-wave) is not detected by the atrial channel, a stimulating pulse will be delivered to depolarize the atrium to cause atrial contraction. Following either a detected P-wave or an atrial pacing pulse, the ventricular channel attempts to detect a depolarization signal in the ventricle, known as an R-wave. If no R-wave is detected within a defined atrial-ventricular interval (AV interval, also referred to as AV delay), a stimulation pulse is delivered to the ventricle to cause ventricular contraction. In this way, rhythmic dual chamber pacing is achieved by coordinating the delivery of ventricular output in response to a sensed or paced atrial event.

It is known that the AV delay setting during dual chamber pacing can have profound effects on hemodynamic function, particularly in patients suffering from congestive heart failure. Extreme differences in cardiac output can result from different AV delay settings. The optimal setting varies between individuals and can range from 50 ms to 200 ms. Determining the optimal setting is often difficult since a number of physiological factors influence the hemodynamic function, and hemodynamic measurements required to determine the optimal setting can be costly, time-consuming, and are often invasive with additional inherent risks.

One approach to optimizing the AV delay involves incorporating in the pacemaker system implantable physiological sensors that are capable of detecting a signal that is indicative of the hemodynamic function of the heart. The AV delay can then be adjusted so that the physiological signal measured indicates maximized hemodynamic function. This approach however requires one or more additional sensors, added hardware circuitry, and additional processing time in order to determine the optimal AV delay. Furthermore, the physiological response to a change in AV delay may not be instantaneous but more likely occurs over an extended period of time. Thus, determining the optimal setting may require testing several settings after extended periods of time during which the patient is not receiving optimal stimulation therapy.

In the majority of individuals, the most effective heartbeat is triggered by the patient's own spontaneous pacemaker. The electronic stimulation device is intended to fill in when the patient's spontaneous pacemaker fails or when the heart's conduction system fails. In a large number of heart failure patients, natural conduction through the atrioventricular node and the bundle of His are intact. Disruption of ventricular rhythm in these patients is the result of conduction disorders residing in the left and/or right bundle branches.

Dilatation of the heart due to congestive heart failure (CHF) has been associated with delayed conduction through the ventricles. This delayed conduction exacerbates the hemodynamic inefficiency of the failing heart because of the resulting poor synchronization of the heart chambers.

Direct stimulation of the His Bundle has been found to provide hemodynamic improvement in patients suffering from dilated cardiomyopathy but having normal ventricular activation. Reference is made to Deshmukh P. et al., "Permanent, Direct His-Bundle Pacing—A New Approach to Cardiac Pacing in Patients With Normal His-Pukinjie Activation," Circulation, 2000;101(8)869-77, Feb. 29, 2000. This result supports the hypothesis that the natural conduction system, when intact, can provide hemodynamically optimal depolarization timing of the heart chambers.

What is needed, therefore, is a cardiac stimulation device capable of delivering ventricular stimulation according to the optimal timing dictated by the heart's own conduction system. It would be desirable, in an implantable dual chamber or multi-chamber cardiac stimulation device, to detect the conduction signal that is naturally conducted through the atrioventricular node and into the His Bundle and trigger ventricular stimulation delivery based on this detected conduction signal.

SUMMARY OF THE INVENTION

The present invention addresses this need by providing a cardiac stimulation device and leads, with an associated method for detecting a conduction signal from the His Bundle, and upon this detection, delivering ventricular stimulation to the right and/or left ventricles. According to one embodiment, the system and method of the present invention advantageously deliver ventricular stimulation at an interval following atrial depolarization that is optimally triggered by the functioning portion of the natural conduction system of the heart, and bypasses the dysfunctional portion of the ventricular conduction system to re-establish rhythmic ventricular contractions with the benefit of efficient hemodynamic output.

A preferred embodiment of the present invention provides an implantable cardiac stimulation device equipped with cardiac data acquisition capabilities. The stimulation device includes a control system for controlling the operation of the device; a set of leads with appropriately positioned electrodes for receiving cardiac signals and for delivering atrial and ventricular stimulation pulses; a set of sensing circuits comprised of sense amplifiers for sensing and amplifying the cardiac signals including a modern low noise amplifier used to sense (and optionally to stimulate the His Bundle) and amplify the conduction signal arising from the His Bundle; a sampler, such as an A/D converter for sampling cardiac signals; an averager capable of determining a moving average of a sampled signal; pulse generators for generating atrial and ventricular stimulation pulses; and an impedance measuring circuit for performing a variety of impedance measurements including a tissue impedance measurement used in locating the His Bundle.

In addition, the stimulation device includes a memory for storing operational parameters for the control system, such as cardiac signal sampling parameters and cardiac signal samples. The device also includes a telemetry circuit for communicating with an external programmer. In the preferred embodiment, the stimulation device further includes a physiological sensor of metabolic demand, such as an activity sensor or a minute volume sensor, that provides feedback to the control system which in turn controls the stimulation rate such that the measured metabolic need is met.

The present invention also provides a His Bundle lead. The His Bundle lead includes a tip electrode at the distal end of the lead for sensing His Bundle conduction signals. The tip electrode is provided with an active fixation device for securing the tip electrode to the His Bundle tissue. The tip electrode also includes a non-traumatic conductive surface used to map the location of the His Bundle prior to fixing the tip electrode in the endocardial tissue. It would also elute an acute anti-arrhythmia drug such as lidocaine and/or an anti-inflammatory agent, to reduce the early PVCs that can be caused by the trauma of the lead implantation.

In an exemplary preferred embodiment, the non-traumatic conductive surface is provided as a mapping collar that functions as a source electrode in performing a tissue impedance measurement for locating the His Bundle during the implantation procedure of the stimulation device and His Bundle lead. The His Bundle lead may further include a ring electrode located between approximately 2 mm and 30 mm, but preferably 10 mm, from the tip electrode to be used in bipolar sensing.

During the implantation procedure, the His Bundle lead is advanced into the right atrial chamber and, when the His electrode is positioned proximate the His Bundle tissue, as indicated by an impedance measurement approximately equal to an expected His Bundle tissue impedance, the active fixation electrode is secured in the His Bundle tissue.

When operating according to a preferred embodiment, the stimulation device control system detects an atrial event, either a sensed atrial P-wave or an atrial stimulation pulse, and initiates a His Bundle signal sensing window beginning almost immediately after the atrial event and extending a predefined amount of time, typically 200 ms.

During the sensing window, the His Bundle signal received through the His Bundle lead is sampled and a moving average is calculated to determine a signal peak. Detection of a His Bundle signal peak triggers ventricular stimulation. Ventricular stimulation may be delivered to the right ventricle, the left ventricle, or both ventricles.

The present invention is particularly advantageous for patients with congestive heart failure (CHF) and having normal conduction paths through the AV node and His Bundle but delayed conduction through the bundle branches or the Purkinje system. Such patients tend to benefit from stimulating the left ventricle (via a lead positioned through the coronary sinus with its electrode(s) in a coronary vein overlying the left ventricle) and the right ventricle almost simultaneously. By sensing the His Bundle signal, the stimulation device can deliver biventricular stimulation with optimal AV delays. The delay from the detected His (or His Bundle) signal to the right ventricular stimulation and the delay from the detected His signal to the left ventricular stimulation may be the same or may be programmable values selected by the clinician in order to achieve a desired synchronization between the left and right ventricular contractions.

In an alternative embodiment, if no His signal is detected, ventricular stimulation may be delivered directly to the His Bundle using the His Bundle lead. This alternative embodiment is beneficial to patients having intact conduction below the level of the His Bundle and having intermittent or partial atrioventricular block. When the atrial depolarization is not conducted through the atrioventricular node, the His Bundle lead may be used to deliver stimulation to depolarize the His Bundle. A depolarization of the His Bundle will then be conducted through the ventricles via the left and right bundle branches and the Purkinje fibers to cause ventricular contraction.

The system and method of the present invention thus provide ventricular stimulation optimally timed following an atrial event according to the heart's natural conduction timing. This optimized ventricular stimulation is accomplished without requiring lengthy testing procedures to determine an optimal AV delay and does not require complex physiological sensors, hardware, or processing algorithms. Patients suffering from congestive heart failure with intact atrioventricular nodal conduction will benefit from improved synchrony of ventricular contractions according to the heart's natural conduction timing. Patients suffering from intermittent atrioventricular nodal block may benefit from His Bundle stimulation with the stimulation device, by providing a bypass of the block and delivering the ventricular stimulation via the remaining intact conduction pathways.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

The present invention is directed at providing a method and apparatus for delivering ventricular stimulation at an optimal time delay following atrial depolarization based upon detecting a conducted signal in the His Bundle. One embodiment of the present invention may be implemented in either a dual chamber or multi-chamber cardiac stimulation device. In a preferred embodiment, the present invention is implemented in a rate-responsive multi-chamber cardiac stimulation device such as the stimulation device 10 depicted in FIG. 1.

Figure 1:
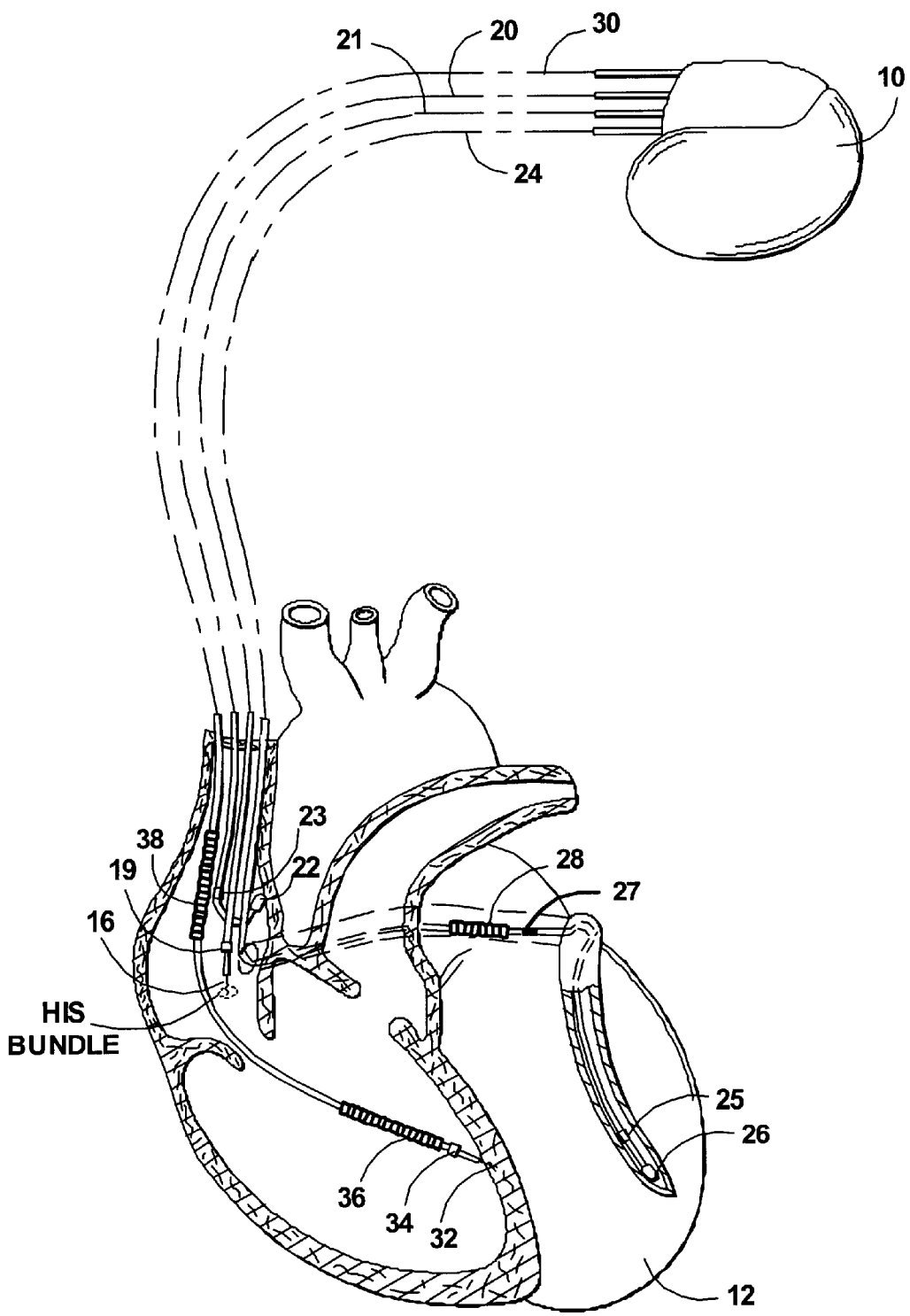
FIG. 1 is a simplified, partly cutaway view illustrating an implantable stimulation device in electrical communication with at least four leads, including a His Bundle lead, implanted into a patient's heart for delivering multi-chamber stimulation and shock therapy.

With reference to FIG. 1, the stimulation device 10 is shown in electrical communication with a patient's heart 12 by way of four leads, 20, 21, 24, and 30 and suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage or atrial septum.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode within the coronary veins overlying the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus which overlies the left ventricle.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. In another embodiment, an additional electrode for providing left ventricular defibrillation shocking therapy may be included in the portion of the lead overlying the left ventricle, adjacent to the ring electrode 25.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

The stimulation device 10 is further connected to a His Bundle lead 21 having a His tip electrode 16, such as a helical active fixation device and a His ring electrode 19 located approximately 12 mm proximal from the His tip electrode 16. The His Bundle lead 21 is transvenously inserted into the heart 12 so that the His tip electrode 16 may be positioned in the tissue of the His Bundle. Accordingly, the His Bundle lead 21 is capable of receiving depolarization signals propagated in the His Bundle or delivering stimulation to the His Bundle, creating a depolarization that can be propagated through the lower conductive pathways of the right and left ventricles (i.e., the right and left bundle branches and Purkinje fibers).

The His Bundle lead 21 will be described in greater detail in conjunction with FIGS. 4 and 5.

Figure 2:
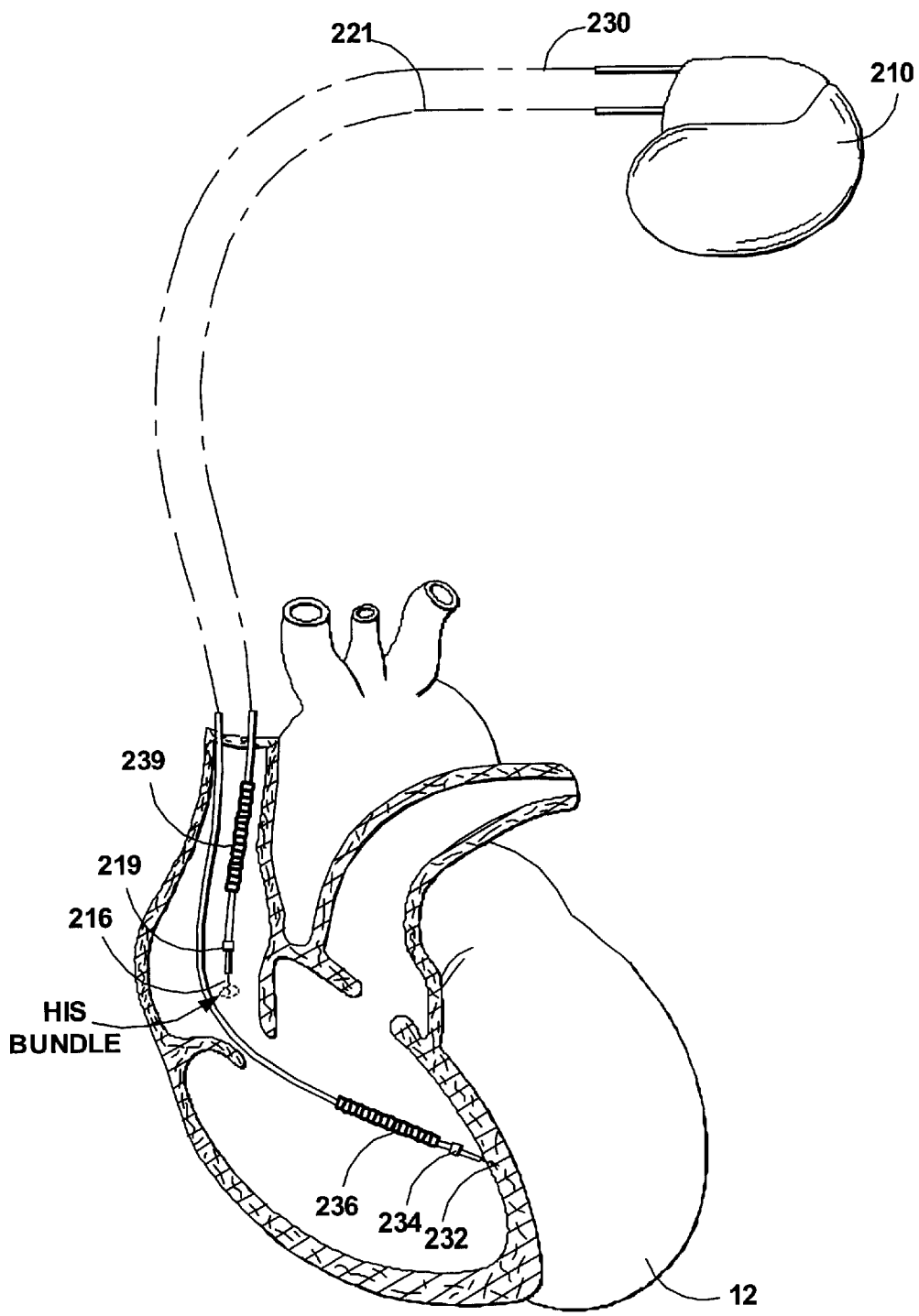
FIG. 2 is a simplified, partly cutaway view illustrating an alternative design of an implantable stimulation device, shown implanted into the right chambers of the patient's heart for delivering dual-chamber stimulation and shock therapy.

An alternative embodiment of the present invention is shown in FIG. 2 in which a dual chamber stimulation device 210 is in communication with one atrium, one ventricle, and the His Bundle. Though not explicitly illustrated in FIG. 2, a right atrial lead 20 (shown in FIG. 1) can be optionally included. The stimulation device 210 maintains communication with the right atrium of the heart 12 via a right atrial lead 20 having at least an atrial tip electrode 22 and an atrial ring electrode 23, that is implanted in the patient's right atrial appendage as described earlier in connection with FIG. 1, and a SVC coil electrode 239.

A His Bundle (or His) lead 221, having a His tip electrode 216 and a His ring electrode 219, is positioned such that the His tip electrode 216 is proximate the His Bundle tissue. The stimulation device 210 is also shown in FIG. 2 to be in electrical communication with the patient's heart 12 by way of a right ventricular lead 230 having, in this embodiment, a right ventricular tip electrode 232, a right ventricular ring electrode 234, and a right ventricular coil electrode 236.

Figure 3:
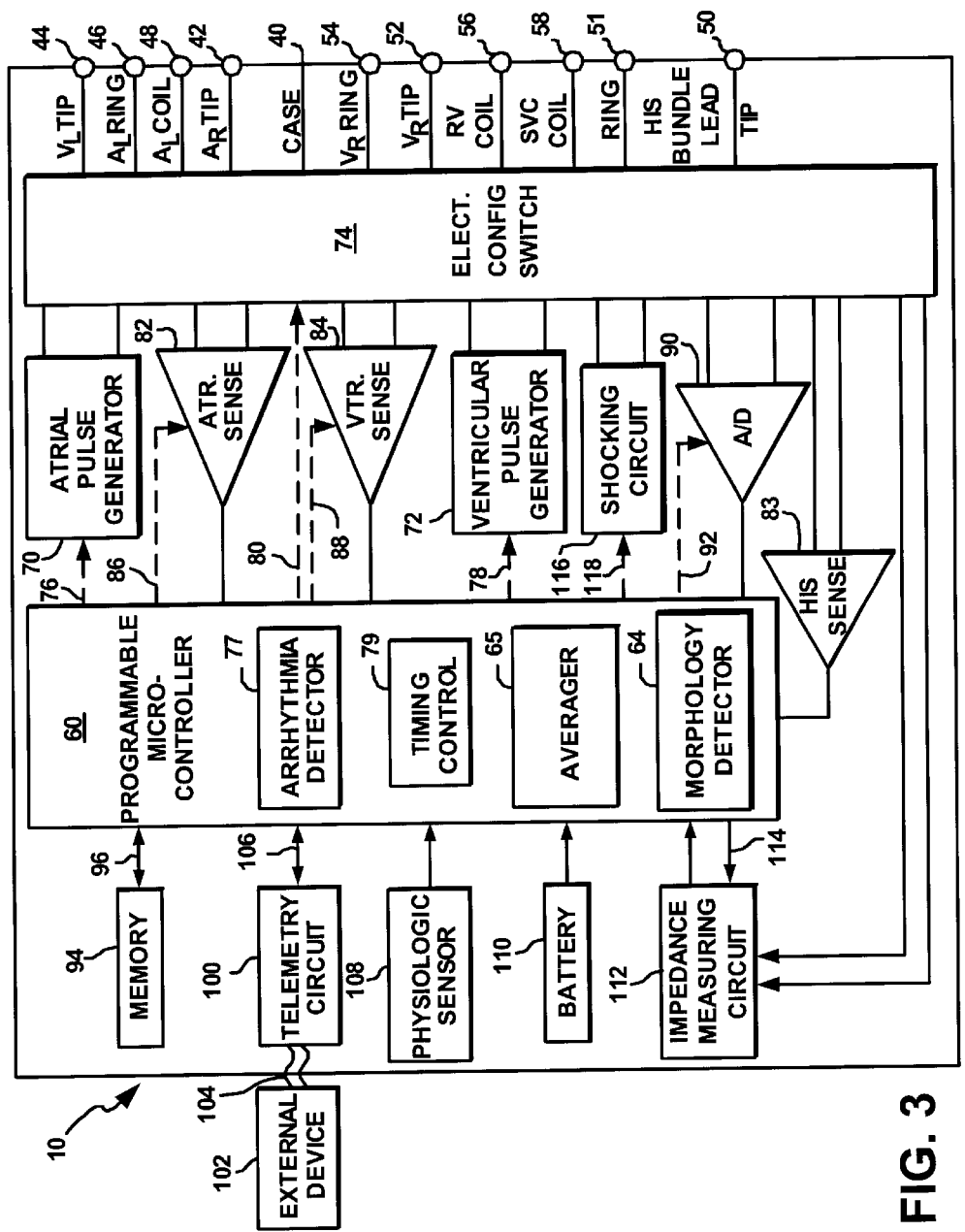
FIG. 3 is a functional block diagram of the multi-chamber implantable stimulation device of FIG. 1, illustrating the basic elements that provide pacing stimulation, cardioversion, and defibrillation in four chambers of the heart.

Referring now to FIG. 3, there is illustrated a simplified block diagram of the multi-chamber implantable stimulation device 10 of FIG. 1, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 3, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38 (FIG. 1), for shocking purposes. The housing 40 further includes a connector (not shown) having a plurality of terminals, 42, 44, 46, 48, 52, 54, 56, 58, 50, and 51 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 (FIG. 1).

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively (FIG. 1).

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively (FIG. 1).

To achieve His Bundle sensing, or sensing and stimulation, the connector further includes a His Bundle lead tip terminal 50 and a His Bundle lead ring terminal 51 which are adapted for connection to the His tip electrode 16 and the His ring electrode 19, respectively (FIG. 1).

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 3, an atrial pulse generator 70 and a ventricular pulse generator 72 generate pacing stimulation pulses for delivery by the right atrial lead 20, the right ventricular lead 30, the coronary sinus lead 24, and/or the His Bundle lead 21 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses. As used herein, the shape of the stimulation pulses is not limited to an exact square or rectangular shape, but may assume any one of a plurality of shapes which is adequate for the delivery of an energy pulse, packet, or stimulus.

The microcontroller 60 further includes timing control circuitry 79 which is used to control the timing of such stimulation pulses (e.g., pacing rate) as well as to keep track of the timing of refractory periods, blanking intervals, noise detection windows, evoked response windows, alert intervals, marker channel timing, etc., which is well known in the art.

According to one embodiment of the present invention, timing control circuitry 79 also controls the onset and duration of a His signal sensing window during which a depolarization signal conducted through the atrioventricular node to the His Bundle can be detected. Timing control circuitry 79 also controls a timing delay provided after a detected His signal detection, prior to the delivery of a right and/or left ventricular stimulation pulse.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

According to one embodiment of the present invention, a His sensing circuit 83 is selectively coupled to the His Bundle lead 21 for detecting the presence of a conducted depolarization arising in the atria and conducted to the bundle of His via the atrioventricular node. As used herein, each of the atrial sensing circuit 82, the ventricular sensing circuit 84, and the His sensing circuit 83, includes a discriminator, which is a circuit that senses and can indicate or discriminate the origin of a cardiac signal in each of the cardiac chambers.

Each sensing circuit, 82, 83 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation.

The outputs of the atrial, His, and ventricular sensing circuits, 82, 83 and 84, respectively, are connected to the microcontroller 60 which, in turn, is able to trigger or inhibit the atrial and ventricular pulse generators, 70 and 72, respectively, in a demand fashion in response to the absence or presence of cardiac activity in the appropriate chambers of the heart.

The sensing circuits, 82, 83, and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits 82 and 86.

For arrhythmia detection, the stimulation device 10 includes an arrhythmia detector 77 that utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to the inputs of an analog-to-digital (A/D) data acquisition system 90 represented by an A/D converter. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the His Bundle lead 21, the coronary sinus lead 24, and the right ventricular lead 30 through the switch 74 to sample cardiac signals across any pair of desired electrodes.

In a preferred embodiment, the data acquisition system 90 is coupled to microcontroller 60, or to other detection circuitry, for detecting a desired feature of the His Bundle signal. In one embodiment, an averager 65 is used to determine a sliding average of the His Bundle signal during a His signal sensing window using known or available signal averaging techniques.

Advantageously, the data acquisition system 90 may be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. Preferably, a capture threshold search is performed at least once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin can be automatically or programmably added to the capture threshold.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, stimulation delays, etc.) at which the atrial and ventricular pulse generators, 70 and 72, generate stimulation pulses.

A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any suitable sensor may be used which is capable of sensing a physiological parameter which corresponds to the exercise state of the patient. The type of sensor used is not critical to the present invention and is shown only for completeness.

The stimulation device additionally includes a battery 110 which provides operating power to all of the circuits shown in FIG. 3. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

The device 10 is shown in FIG. 3 as having an impedance measuring circuit 112 which is enabled by the microcontroller 60 via a control signal 114. The known uses for an impedance measuring circuit 112 include, but are not limited to, lead impedance surveillance during the acute and chronic phases for detecting proper lead positioning or dislodgement; detecting operable electrodes and conductors; and automatically switching to an operable pair if dislodgement or electrical disruption occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

According to one embodiment of the present invention, the His tip electrode 16 and His ring electrode 19 may be selectively coupled via switch 74 to the impedance measuring circuit 112 for performing a tissue impedance measurement. The tissue impedance measurement is made to determine the location of the His Bundle as the His tip electrode 16 or mapping collar 418 as shown in FIG. 4, or sensing electrodes 420, 421, 422, 423 as shown in FIG. 5, is advanced along the endocardial surface of the right atrium. A method for performing this tissue impedance measurement using the His Bundle lead 21 will be described further in conjunction with FIG. 6.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asychronously (since R-waves may be too disorganized), and pertaining exclusively to the treatment of fibrillation. Accordingly, the microcontroller 60 is capable of controlling the synchronous or asynchronous delivery of the shocking pulses.

Figure 4:
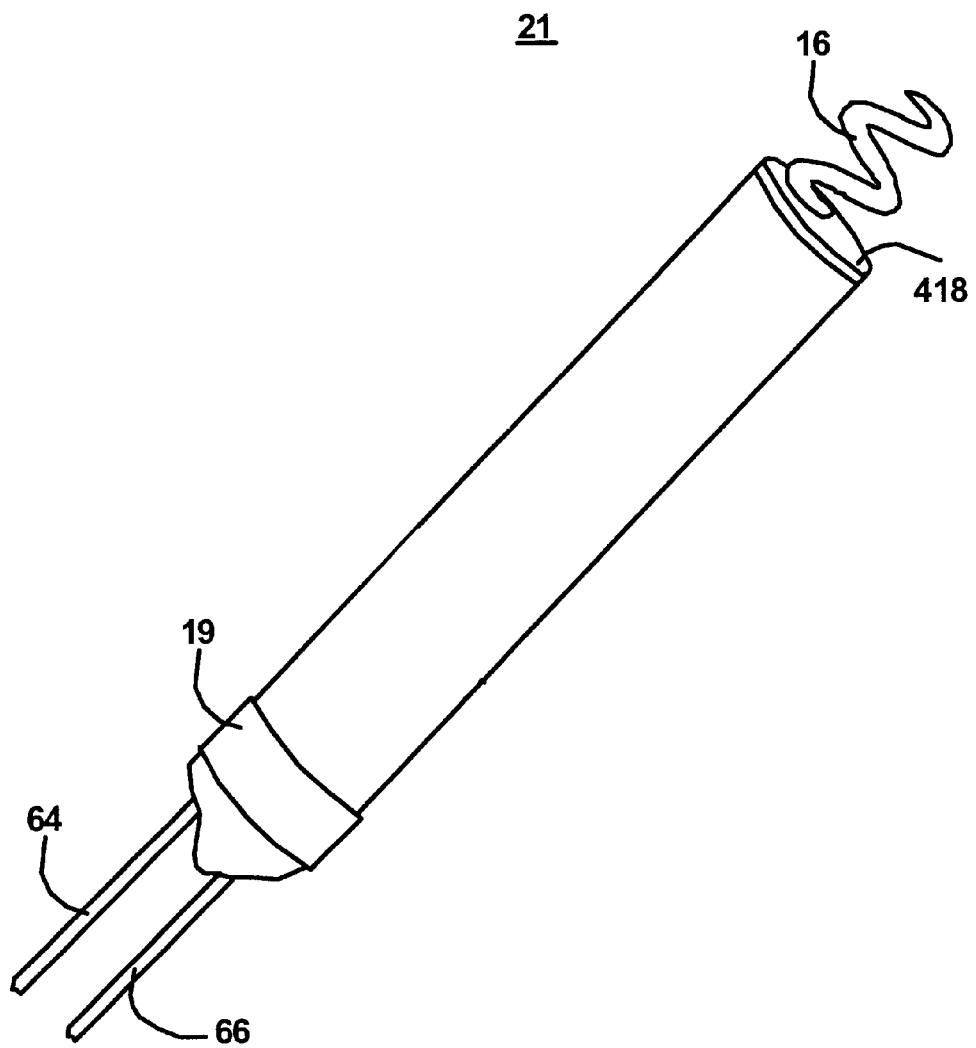
FIG. 4 is a partly fragmentary illustration of the distal end of the His Bundle lead for use with the stimulation device of FIG. 3, depicting a tip electrode with an active fixation device and a non-traumatic conductive surface, and a ring electrode.

A more detailed illustration of the His Bundle lead 21 is shown in FIG. 4. At the distal end of the lead 21 is the His Bundle tip electrode 16. The His Bundle tip electrode 16 is, or includes, an active fixation device, preferably a helical, "screw-in," device that allows stable fixation of the electrode in the His Bundle tissue.

The distal end of the His Bundle lead 21 is further provided with a non-traumatic conductive surface (also referred to herein interchangeably as mapping collar) 418. The non-traumatic conductive surface 418 is advantageously used to make electrical measurements that indicate the location of the His Bundle without having to anchor the His Bundle tip electrode 16 into the endocardial tissue. The non-traumatic conductive surface 418 and the His Bundle tip electrode 16 are electrically coupled within the lead body of the His Bundle lead 21 and together form one conductive element for the purposes of sensing, stimulation, and impedance measurements. Drugs, for example an acute anti-arrhythmic drug such as lidocaine and/or an anti-inflammatory agent such as dexamethazone sodium phosphate, can be stored, for example, within a reservoir (not shown) at the base of the His Bundle tip electrode 16 for local dispensation.

The His Bundle lead 21 is also provided with a His ring electrode 19. The His ring electrode 19 is preferably spaced between approximately 2 mm and 30 mm, but preferably 10 mm, from the His tip electrode 16. The His ring electrode 19 may function as the return electrode during bipolar sensing, stimulation or impedance measurement operations.

The His tip electrode 16 and the His ring electrode 19 are each connected to flexible conductors 64 and 66, respectively, running the entire length of the His Bundle lead 21. The flexible conductor 64 is connected to the His tip electrode 16 and is electrically insulated from the flexible conductor 66 by a layer of insulation. The conductor 66 is connected to the His ring electrode 19. The flexible conductors 64 and 66 serve to electrically couple the His ring electrode 19 and the His tip electrode 16 to the His ring electrode terminal 51 and the His tip electrode terminal 50, respectively. One embodiment of the His Bundle lead 21 is available from St. Jude Medical CRMD as lead model No. 1488T.

Figure 5:
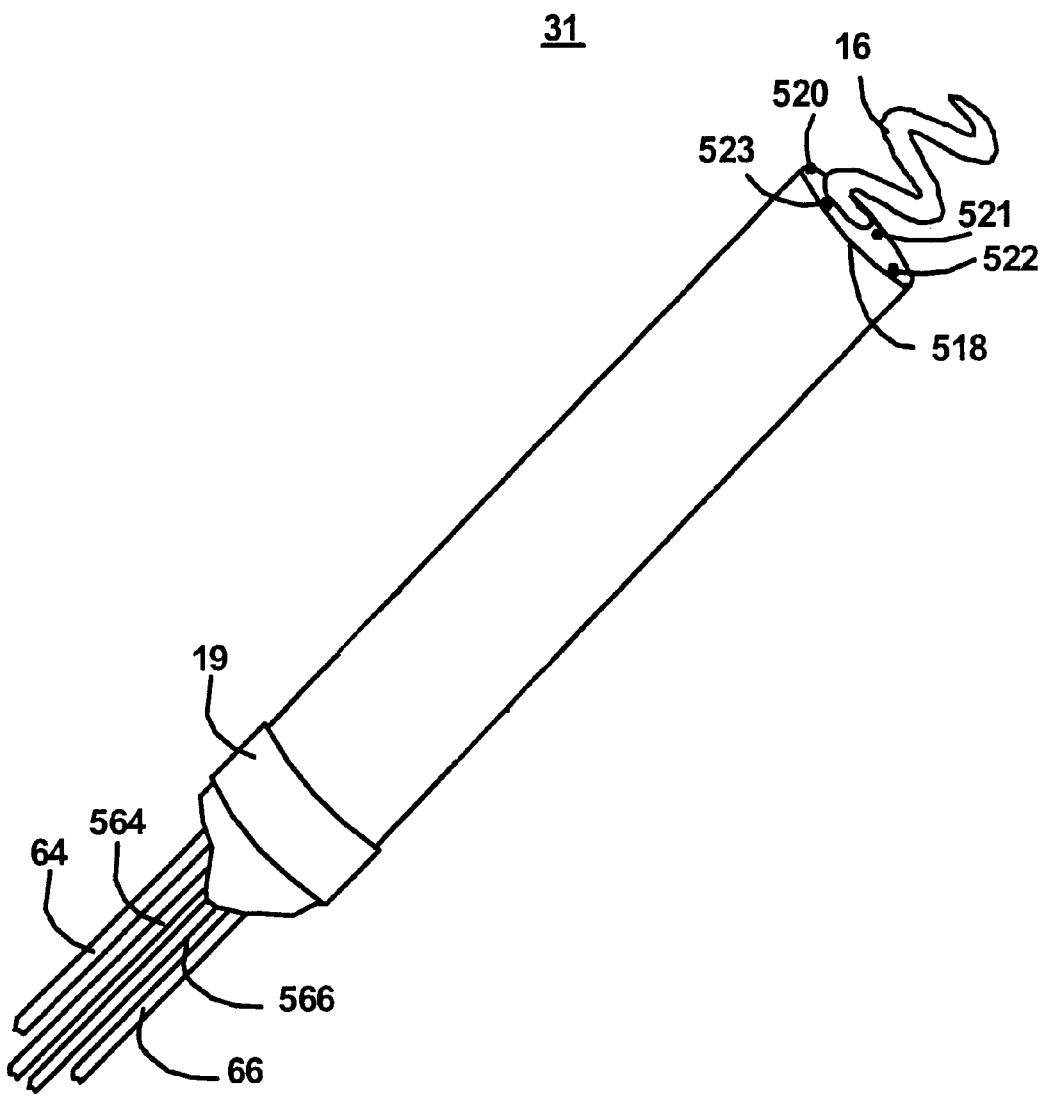
FIG. 5 is a partly fragmentary illustration of the distal end of another His Bundle lead for use with the stimulation device of FIG. 3, depicting a tip electrode with an active fixation device and a non-traumatic conductive surface, a ring electrode, and a four conductive sensing electrodes.

FIG. 5 illustrates an In an alternative His lead 31 that is generally similar in function and design to the His lead 21. The His lead 31 is provided with a His tip electrode 16 that includes multiple, round, closely-spaced conductive surfaces 520, 521, 522, 523 that are arranged on a distal most face 518 of the lead 31, directly facing the His Bundle tissue. Though four round conductive surfaces 520, 521, 522, 523 are shown herein as being uniformly distributed around the His tip electrode 16 and are electrically separated from each other by insulating material, it should be clear that a different number of conductive surfaces may alternatively be selected.

In one embodiment, a conductive surface, e.g. 520 is connected to its own flexible conductor, e.g. 564 that extends along the length of the His Bundle lead 31. The remaining conductive surfaces 521, 522, 523 are electrically connected together and are also connected to a flexible conductor 566 that extends along the length of the His Bundle lead 31. The flexible conductors, e.g. 526, 527 are insulated from each other.

In this embodiment, the device 10 includes two separate connection terminals, one for each of the two flexible conductors 564, 566, that are further connected to switch 74. The two flexible conductors 564, 566 can then be selectively connected as desired to the His sensing circuit 83, ventricular pulse generator 72, or impedance measuring circuit 112 for sensing, stimulating, and measuring tissue impedance at the site of the His Bundle (FIG. 3).

Using the lead 31, it is possible to effect stimulation with the His tip electrode 16 and the His ring electrode 19, and to effect sensing with the conductive surfaces 520, 521, 522, 523. According to another design, the sensing is effected by the conductive surfaces 520, 521, 522, 523 and stimulation is effected by means of the leads other than the His lead 31, for example the right atrial lead 20. For more details regarding a heart electrode equipped with multiple conductive surfaces, reference is made to U.S. Pat. Nos. 5,306,292 and 5,645,580, which are incorporated herein by reference.

During the implantation procedure, the His Bundle lead 21 of FIG. 4 (or the His Bundle lead 31 of FIG. 5) is introduced transvenously into the right atrium. It is then gradually advanced with the His tip electrode 16 in contact with the endocardial tissue. Electrical measurements are made continuously as the His tip electrode 16 is advanced to determine the location of the His Bundle. The non-traumatic conductive surface 418 advantageously provides electrical contact with the endocardial tissue thereby allowing electrical measurements to be performed without having to fix the His tip electrode 16 into the endocardial tissue using the His Bundle tip electrode 16.

Figure 6:
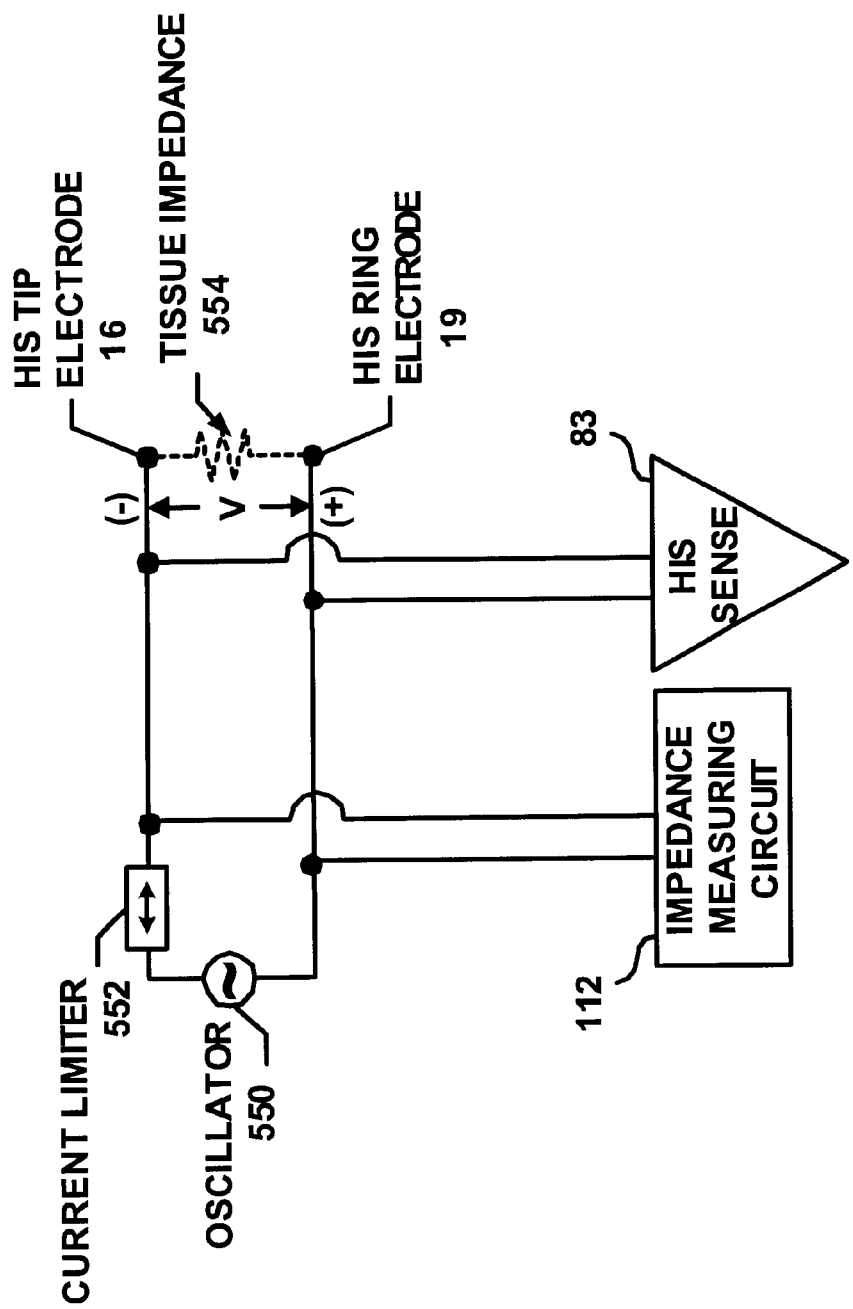
FIG. 6 is an equivalent circuit diagram illustrating a tissue impedance measurement method using the lead of FIG. 4 and the stimulation device of FIG. 3 for locating the His Bundle.

In a preferred embodiment, tissue impedance measurements are made in order to locate the His Bundle. The equivalent circuit diagram depicted in FIG. 6 represents a model by which a tissue impedance measurement can be made using the His Bundle lead 21 of FIG. 4. An excitation current is applied through the His tip electrode 16. The excitation current is preferably provided as a current limited high-frequency alternating current signal produced by a 30kHz oscillator 550 passing through a current limiter 552. A voltage signal can then be measured between the His tip electrode 16 (or the non-traumatic conductive surface 418) and the His ring electrode 19 in a bipolar fashion. The voltage signal is related to the supplied current and the tissue impedance 554 associated with the tissue in contact with the His tip electrode 16. Thus, the measured voltage signal is processed by the impedance measuring circuit 112 to determine the impedance of the tissue in contact with His tip electrode 16. The impedance equals the voltage divided by the current.

Right atrial tissue impedance is expected to be approximately twice that of the His Bundle. Using the foregoing measurement method, the right atrial tissue impedance is typically on the order of 1200 to 1500 ohms, whereas the His Bundle tissue impedance is typically on the order of 600 to 800 ohms. Other impedance values can be obtained using different measurement techniques. Thus, as the His Bundle lead 21 is advanced in the right atrium, a large decrease in measured tissue impedance 554, of approximately 50%, indicates that the His Bundle tip electrode 15 is proximate the His Bundle.

The His Bundle tip electrode 16 may then be secured in the His Bundle thereby anchoring the His tip electrode 16 in contact with the His Bundle tissue. The electrogram signal arising from the His Bundle can then be received by the His sensing circuit 83. Preferably, a bypass filter (not shown) that allows signals ranging between 30 Hz and 200 Hz to be received is used to block the high frequency alternating current excitation signal produced by the oscillator 550.

Figure 7:
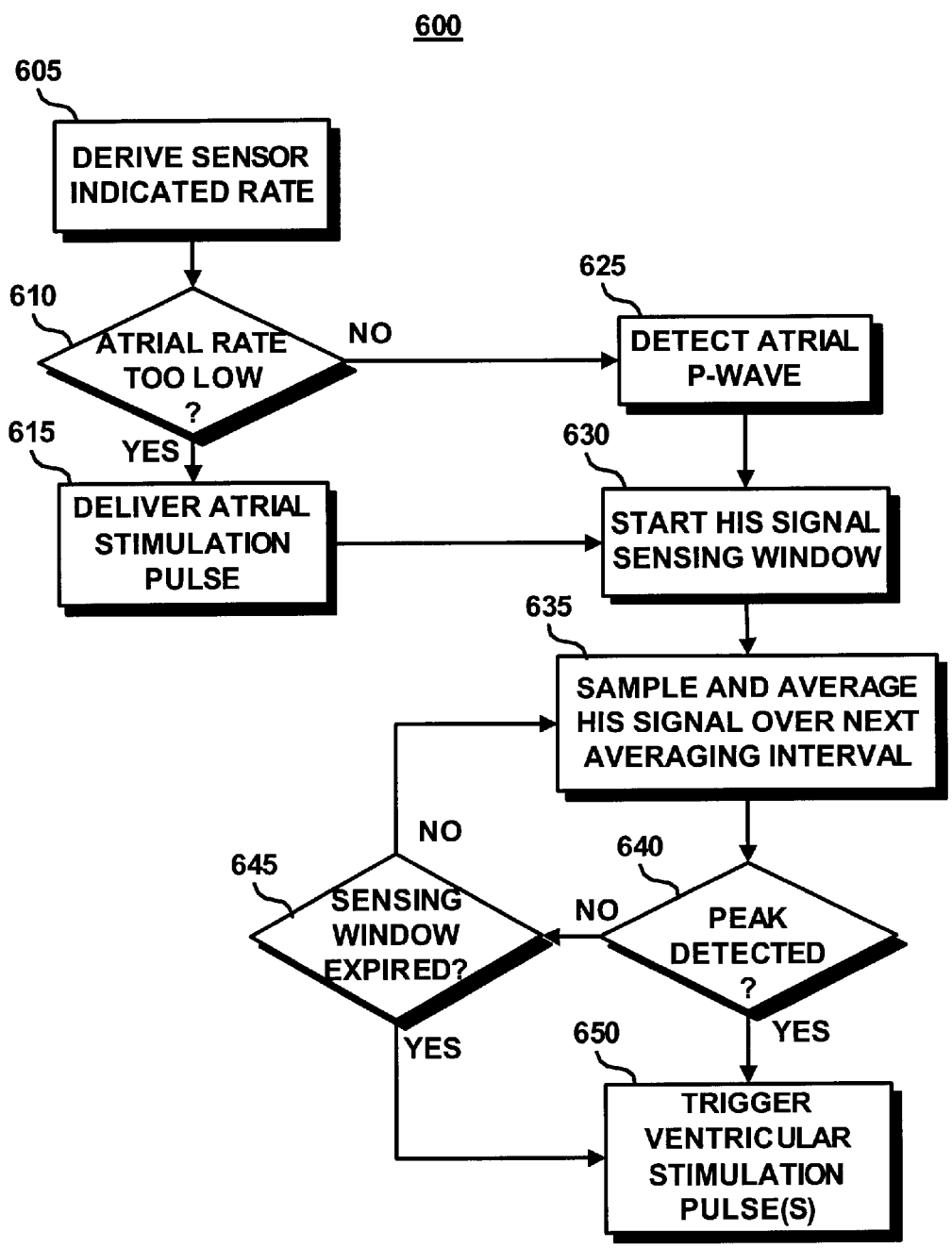
FIG. 7 is a flow chart providing an overview of the methods implemented by the stimulation device of FIG. 3, for providing ventricular stimulation at an optimal time after an atrial P-wave based on the detection of a His signal peak using the lead depicted in FIG. 4.

FIG. 7 illustrates a flow chart of an operation implemented by the device stimulation 10 according to the present invention. In this flow chart, and other flow charts presented herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The algorithm of FIG. 7 represents a method 600 for triggering ventricular stimulation based on the detection of the His Bundle signal. Beginning at step 605, microcontroller 60 determines the rate indicated by the physiologic sensor 108 that would meet the patient's current metabolic demand. If method 600 determines at decision step 610 that the sensed atrial rate is lower than the metabolic need as indicated by the physiological sensor 108, an atrial stimulation pulse is delivered at step 615. The His signal sensing window is initiated after the atrial stimulation pulse at step 630. The onset and duration of the His signal sensing window following an atrial stimulation pulse are preferably programmable settings. If the intrinsic atrial rate adequately meets the physiologic sensor indicated rate as determined at decision step 610, then a His signal sensing window is initiated at step 630 after detection of the next P-wave at step 625. The His signal sensing window should typically begin immediately upon detection of the P-wave, but the onset and duration of the His signal sensing window are preferably both programmable settings and may be the same or different than the His signal sensing window following an atrial stimulation pulse. The appropriate duration of the His signal sensing window may vary between patients and could range from approximately 50 ms to approximately 200 ms.

During the His signal sensing window, the His Bundle signal is sampled, as indicated at step 635, by His sensing circuit 83 at a predetermined sampling frequency that may range between approximately 50 Hz and 2 kHz. The sampled signal data is received by microprocessor 60 to be averaged according to modern signal averaging methods by averager 65.

Preferably, a "sliding" average of the His Bundle signal is obtained at step 635. A "sliding" average is determined by averager 65 by averaging the sampled signal points over an averaging interval of, for example, approximately 0 to 150 ms. The sliding average is calculated on a "first-in-first-out" basis meaning that a new sampling point replaces the oldest sampling point in calculating the sliding average.

When microprocessor 60 detects a peak in the sliding average of the His Bundle signal, as determined at decision step 640, a right ventricular stimulation pulse and/or a left ventricular pulse are triggered at step 650. The right and left ventricular stimulation pulses may be delivered almost immediately (preferably with some delay), or they may be delivered after a programmed delay following the detected His signal peak. The delay after the detected peak until right ventricular stimulation pulse delivery may be the same or different than the delay until left ventricular stimulation pulse delivery. The right and left ventricular stimulation pulses are generated by ventricular pulse generator 72 and delivered via the desired pair of electrodes using right ventricular lead 30 and/or coronary sinus lead 24, respectively.

If microprocessor 60 does not detect a peak of sufficient amplitude and the His signal sensing window expires as determined at step 645, the right and left ventricular stimulation pulses are delivered upon expiration of the His signal sensing window at step 650. Otherwise, the His Bundle signal continues to be sampled and averaged at step 635 until a peak is detected or until the sensing window expires.

Thus, according to method 600 illustrated in FIG. 7, ventricular stimulation pulses may be delivered to the right and left ventricles at an optimal time based on the conduction of an atrial depolarization through the atrioventricular node and His Bundle. It is expected that this natural conduction timing is most beneficial to the patient.

In an alternative embodiment, the His Bundle lead 21 may be used for stimulating the ventricles at the site of the His Bundle as well as sensing the His Bundle signal. His Bundle stimulation may be beneficial to patients having intermittent or partial atrioventricular block but intact ventricular conduction pathways below the level of the atrioventricular node. When no His signal is detected due to a return of atrioventricular block, stimulation may be delivered to the His Bundle to depolarize the ventricles. A stimulation pulse delivered by the His Bundle lead 21 that successfully depolarizes the His Bundle will cause the depolarization to be conducted throughout the ventricular chambers via the normal left and right bundle branches and Purkinje fibers.

In this embodiment, if the His signal sensing window expires at step 645, the ventricular stimulation pulse delivered at step 650 of FIG. 7 is delivered by the His Bundle lead 21. The stimulation pulse may be delivered in a unipolar fashion using the His Bundle tip electrode 15 and the device housing 40 or in a bipolar fashion using the His Bundle tip electrode 16 and the His Bundle ring electrode 19. The His Bundle tip electrode 16 and the His Bundle ring electrode 19 are connected according to the selected stimulation polarity via switch 74 to the ventricular pulse generator 72.

It is recognized that the His Bundle signal may be analyzed in numerous ways such that characteristics other than a peak in the sliding average can be used to trigger the delivery of ventricular stimulation pulses. For example, the median or mode of the integrated voltage signal may be determined as the point in time upon which ventricular stimulation is based. The flow chart of FIG. 8 illustrates an alternative method 700 for analyzing the His Bundle signal and triggering ventricular stimulation.

Figure 8:
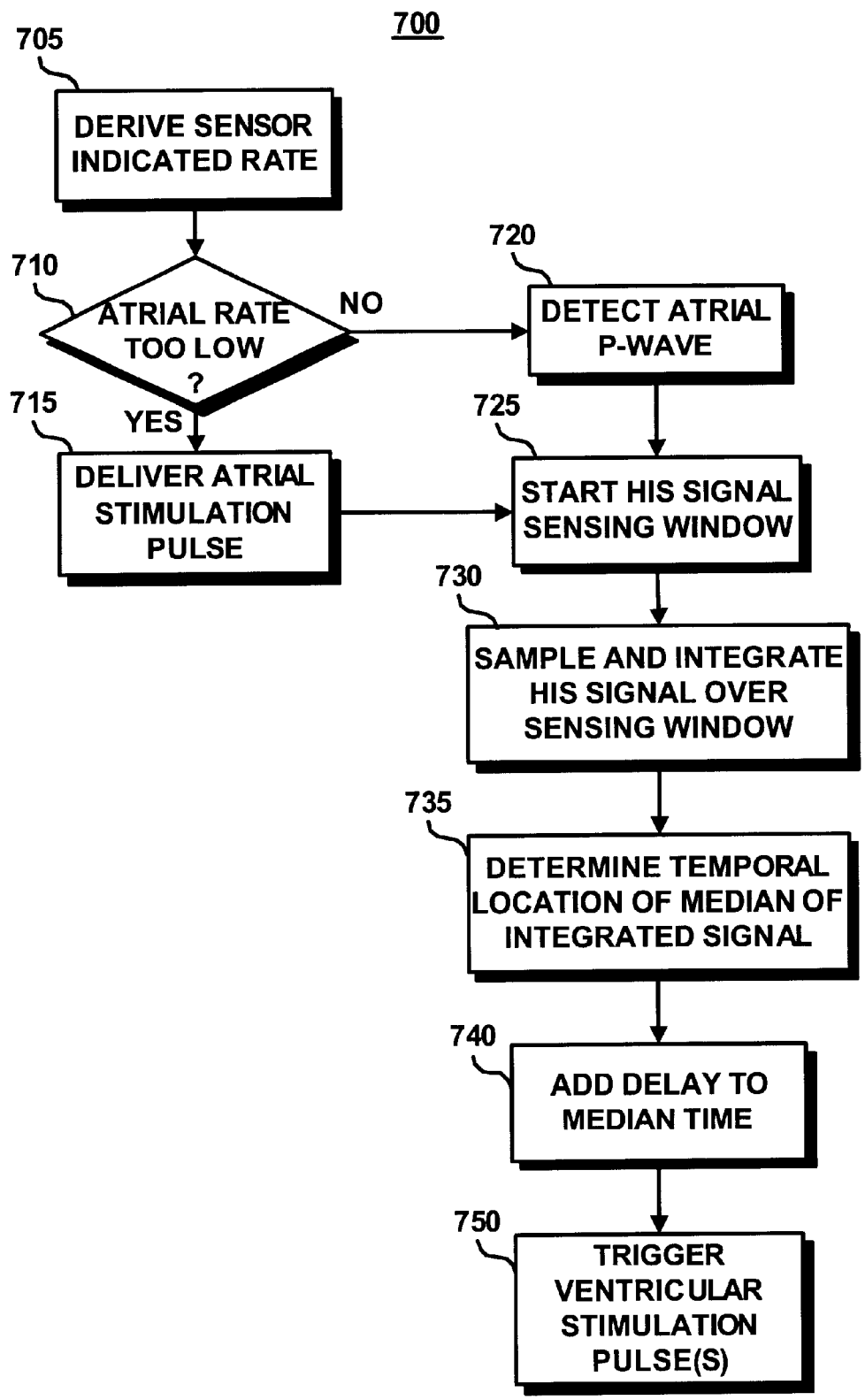
FIG. 8 is a flow chart providing an overview of the operations included in an alternative embodiment of the present invention for providing ventricular stimulation at an optimal time after an atrial P-wave based on the detection of a His signal median using the lead depicted in FIG. 4 and the stimulation device of FIG. 3.

Method 700 of FIG. 8 begins in the same way as the method of FIG. 7. The sensor-indicated rate is determined at step 705 and compared to the atrial rate at step 710. If the atrial rate is too low, an atrial stimulation pulse is delivered at step 715. If the atrial rate is not too low, the atrial P-wave is detected at step 720. Both an atrial stimulation pulse and a sensed atrial P-wave will cause the His signal sensing window to be initiated at step 725. At step 730, the method of FIG. 8 samples and integrates the His signal over the entire duration of the His signal sensing window rather than determining a sliding average as in the method of FIG. 7.

Figure 9:
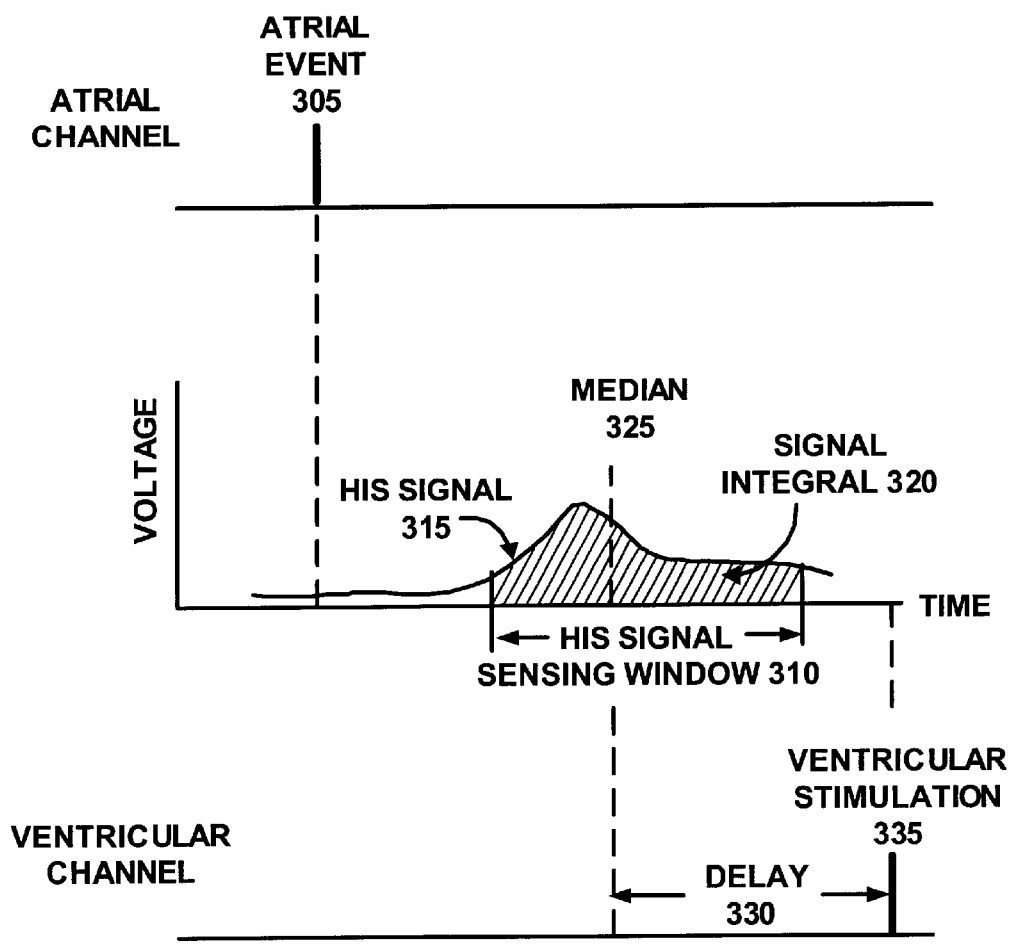
FIG. 9 is a timing diagram depicting a sequence of events that occur during the operations of FIG. 8.

These events are also portrayed in the timing diagram shown in FIG. 9. On the atrial channel, an atrial event 305, either a sensed P-wave or an atrial stimulation pulse, is followed by a His signal sensing window 310. The onset and the duration of the His signal sensing window are predefined, preferably programmable, values which may also depend on whether the atrial event 305 was a stimulation pulse or a sensed P-wave. The His signal 315 is integrated over the entire His signal sensing window 310 to determine the area under the His signal 315 shown as the signal integral 320. The point in time at which half of the area of the signal integral 320 has been reached is then determined by microprocessor 60 as the median 325 of the His signal integral 320.

Thus, at step 735 of FIG. 8, the temporal location of the median 325 of the His signal integral 320 is determined. At step 740, a predefined delay is added to the time at which the median 325 occurred. After the delay expires, ventricular stimulation is delivered at step 750. Ventricular stimulation may be delivered to one or, preferably, both ventricular chambers. Hence, the delay 330 preceding ventricular stimulation 335 shown in FIG. 9 may be a programmable setting with the delay to right ventricular stimulation and the delay to left ventricular stimulation being equal or each uniquely defined.

Thus, a method and apparatus has been provided which deliver ventricular stimulation at an optimal time after an atrial event according to the natural conduction rate of the atrioventricular node and His Bundle. In patients having intermittent of total atrioventricular block, a method and apparatus has been provided which allows stimulation of the His Bundle such that the ventricles are depolarized via the remaining natural conduction system. While the present invention has been described according to specific embodiments, this description is intended for illustration and not limitation. Those skilled in the art may modify features or methods described herein without departing from the scope of the present invention as set forth in the following claims. It will also be appreciated by a person of ordinary skill in the art that the delay should be sufficient to allow the integration of the signal for determining an accurate medium or mode.

What is claimed is:

1. A cardiac stimulation device to deliver ventricular stimulation pulses following an atrial depolarization, comprising:
    a His Bundle sense electrode disposed in proximity to a Bundle of His;
    a stimulation electrode to deliver the ventricular stimulation pulses;
    a sense circuit coupled to the His Bundle sense electrode to detect a conduction signal which is naturally conducted through an AV node into the Bundle of His;
    a timing control circuit coupled to the His Bundle sense electrode and the sense circuit to initiate a His Bundle signal sensing window;
    a sampler to sample the detected conduction signal during the His Bundle signal sensing window; and
    a processor to deliver the ventricular stimulation pulses based on the detected conduction signal.

2. A cardiac stimulation device to deliver ventricular stimulation pulses following an atrial depolarization, comprising:
    a plurality of electrodes including an atrial sense electrode for sensing the atrial depolarization, a His Bundle sense electrode disposed in proximity to a Bundle of His, and a stimulation electrode for delivering the ventricular stimulation pulses;
    a sense circuit, coupled to the His Bundle sense electrode, that detects a conduction signal which is naturally conducted through an AV node into the Bundle of His;
    a timing control circuitry connected to the His Bundle sense electrode and the sense circuit to initiate a His Bundle signal sensing window following the sensing of the atrial depolarization;

a sampler that samples the detected conduction signal during the His Bundle signal sensing window; and a pulse generator, connected to the stimulation electrode, to deliver the ventricular stimulation based on a detected conduction signal.

3. The cardiac stimulation device of claim 2, wherein the His Bundle signal sensing window extends for approximately 200 ms.

4. The cardiac stimulation device of claim 3, wherein the pulse generator generates the ventricular stimulation pulses to a right ventricular chamber.

5. The cardiac stimulation device of claim 3, wherein the pulse generator generates the ventricular stimulation pulses to a left ventricular chamber.

6. The cardiac stimulation device of claim 3, wherein the pulse generator generates stimulation pulses for delivery to the Bundle of His.

7. The cardiac stimulation device of claim 3, wherein the pulse generator generates the ventricular stimulation pulses to at least one of a right ventricular chamber and a left ventricular chamber.

8. The cardiac stimulation device of claim 7, wherein the pulse generator generates a stimulation pulse directly to the Bundle of His to induce ventricular contraction.

9. The cardiac stimulation device of claim 7, wherein the timing control circuitry sets a first AV delay from the detected conduction signal to the delivery of the ventricular stimulation pulse to at least one of the right ventricular chamber and the left ventricular chamber.

10. The cardiac stimulation device of claim 9, further including an averager that determines a moving average of the conduction signal to determine a His signal peak; and
    wherein the pulse generator generates the ventricular stimulation pulse following a detection of the His signal peak.

11. The cardiac stimulation device of claim 9, further including an integrator that determines a median of the conduction signal; and
    wherein the pulse generator generates the ventricular stimulation pulse following a detection of the median.

12. The cardiac stimulation device of claim 2, further including a His Bundle tip electrode secured to the Bundle of His to deliver a stimulation pulse to the Bundle of His.

13. The cardiac stimulation device of claim 12, wherein the His Bundle sense electrode includes a plurality of sense electrodes that are spaced apart in proximity to the His Bundle tip electrode, and that are disposed in contact with the Bundle of His.

14. The cardiac stimulation device of claim 12, further including a mapping collar that is disposed in proximity and is electrically coupled to the His Bundle tip electrode.

15. The cardiac stimulation device of claim 14, wherein the His Bundle sense electrode includes a His Bundle ring electrode that is distally located relative to the mapping collar.

16. The cardiac stimulation device of claim 14 further including a reservoir disposed in proximity to the mapping collar, for storing a medicament.

17. A cardiac stimulation device to deliver ventricular stimulation pulses following an atrial stimulation pulse, comprising:
    a plurality of electrodes including an atrial stimulation electrode for delivering the atrial stimulation pulse, a His Bundle sense electrode disposed in proximity to a Bundle of His, and a ventricular stimulation electrode for delivering the ventricular stimulation pulses;
    a sense circuit, coupled to the His Bundle sense electrode, that detects a conduction signal which is naturally conducted through an AV node into the Bundle of His;
    a timing and control circuit connected to the His Bundle sense electrode and the sense circuit to initiate a His Bundle signal sensing window following a sensing of the atrial stimulation pulse;
    a sampler that samples the detected conduction signal during the His Bundle signal sensing window; and
    a pulse generator, connected to the ventricular stimulation electrode, to deliver the ventricular stimulation pulses based on the defected conduction signal.

18. The cardiac stimulation device of claim 17, wherein the timing control circuitry sets a first AV delay from the detected conduction signal to the delivery of the ventricular stimulation pulse to at least one of a right ventricular chamber and a left ventricular chamber.

19. The cardiac stimulation device of claim 17, wherein the pulse generator generates stimulation pulses for delivery to the Bundle of His.

20. A cardiac stimulation device for delivering ventricular stimulation pulses following an atrial depolarization, comprising:
    an atrial sensing means for sensing the atrial depolarization;
    a His Bundle sensing means disposed in proximity to a Bundle of His;
    a stimulation means for delivering the ventricular stimulation pulses;
    means for detecting a conduction signal which is naturally conducted through an AV node into the Bundle of His;
    a sampler to sample the detected conduction signal; and
    means for delivering the:ventricular stimulation pulses based on the detected conduction signal.

21. The cardiac stimulation device of claim 20, further including a means for initiating a His Bundle signal sensing window following the sensing of the atrial depolarization.

22. The cardiac stimulation device of claim 21, wherein the initiating means sets a first AV delay from the detected conduction signal to the delivery of the ventricular stimulation pulse to at least one of the right ventricular chamber and the left ventricular chamber.

23. A cardiac stimulation device for delivering ventricular stimulation pulses following an atrial stimulation pulse, comprising:
    a His Bundle sensing means disposed in proximity to a Bundle of His;
    a stimulation means for delivering the ventricular stimulation pulses and the atrial stimulation pulse;
    means for detecting a conduction signal which is naturally conducted through an AV node into the Bundle of His;
    a sampler to sample the detected conduction signal; and
    means for delivering the ventricular stimulation pulses based on a delivered atrial stimulation pulse.

24. The cardiac stimulation device of claim 23, further including means for initiating a His Bundle signal sensing window following the delivery of the atrial stimulation pulse; and
    wherein the initiating means sets a first AV delay from the detected conduction signal to the delivery of the ventricular stimulation pulse to at least one of the right ventricular chamber and the left ventricular chamber.

25. A method of delivering ventricular stimulation pulses following an atrial depolarization comprising:
    initiating a IUs Bundle signal sensing window;
    detecting a conduction signal that is naturally conducted through an AV node into a Bundle of His;

sampling the detected conduction signal during the His Bundle signal sensing window; and delivering the ventricular stimulation pulses based on the detected conduction signal.

26. A method of delivering ventricular stimulation pulses following an atrial depolarization, comprising the steps of:

sensing the atrial depolarization;

initiating is Bundle signal sensing window following the sensing of the atrial depolarization;

detecting a conduction signal that is naturally conducted through an AV node into a Bundle of His;

sampling the detected conduction signal during the His Bundle signal sensing window; and delivering a ventricular stimulation pulse based on the detected conduction signal.

27. A The method of claim 26, wherein the step of initiating the His Bundle signal sensing window includes extending the His Bundle signal sensing window for a predetermined length of time.

28. The method of claim 27, wherein the step of extending the His Bundle signal sensing window for a predetermined length of time includes extending the His Bundle signal sensing window for approximately 200 ms.

29. The method of claim 26, wherein the step of delivering the ventricular stimulation pulse includes stimulating a right ventricular chamber.

30. The method of claim 26, wherein the step of delivering the ventricular stimulation pulse includes stimulating a left ventricular chamber.

31. The method of claim 26, wherein the step of delivering the ventricular stimulation pulse includes stimulating a right ventricular chamber and a left ventricular chamber.

32. The method of claim 31, further including setting a first AV delay from the detected conduction signal to the delivery of the ventricular stimulation pulse to the right ventricular chamber.

33. The method of claim 31, further including setting a second AV delay from the method conduction signal to the delivery of the ventricular stimulation pulse to the left ventricular chamber, to achieve synchronization between left and right ventricular contractions.

34. The method of claim 31, wherein if the conduction signal is not detected, delivering a stimulation pulse directly to the Bundle of His to induce ventricular contraction.

35. The method of claim 26, wherein sampling the detected conduction signal during the His Bundle signal sensing window includes calculating a moving average of the conduction signal to determine a His signal peak.

36. The method of claim 35, further including the step of delivering the ventricular stimulation pulse following a detection of the His signal peak.

37. The method of claim 26, wherein sampling the detected conduction signal during the His Bundle signal sensing window includes calculating a median of the conduction signal.

38. The method of claim 37, further including the step of delivering the ventricular stimulation pulse following a detection of the median.

39. A method of delivering ventricular stimulation pulse following an atrial stimulation, comprising the steps of:

delivering the atrial stimulation;

initiating a His Bundle signal sensing window following the delivery of the atrial stimulation;

detecting a conduction signal that is naturally conducted through an AV node into a Bundle of His;

sampling the detected conduction signal during the His Bundle signal sensing window; and delivering a ventricular stimulation pulse based on the detected conduction signal.

40. The method of claim 39, wherein the step of initiating the His Bundle signal sensing window includes extending the His Bundle signal sensing window for a predetermined length of time.

41. The method of claim 39, wherein the step of delivering the ventricular stimulation pulse includes stimulating at least one of a right ventricular chamber and a left ventricular chamber.

42. The method of claim 41, further including setting a first AV delay from the detected conduction signal to the delivery of the ventricular stimulation pulse to the right ventricular chamber; and setting a second AV delay from the detected conduction signal to the delivery of the ventricular stimulation pulse to the left ventricular chamber, to achieve synchronization between left and right ventricular contractions.

43. The method of claim 39, wherein if the conduction signal is not detected, delivering a stimulation pulse directly to the Bundle of His to induce ventricular contraction.

44. The method of claim 39, wherein sampling the detected conduction signal during the His Bundle signal sensing window includes calculating a moving average of the conduction signal to determine a His signal peak; and delivering the ventricular stimulation pulse following a detection of the signal peak.

45. The method of claim 39, wherein sampling the detected conduction signal during the His Bundle signal sensing window includes calculating a median of the conduction singal; and delivering the ventricular stimulation pulse following a detection of the median.

* * * * *